United States Patent
Baker et al.

(10) Patent No.: US 8,455,261 B2
(45) Date of Patent: Jun. 4, 2013

(54) DETECTION OF HALOGENS

(75) Inventors: Derek Martin Baker, Bristol (GB); Sam Olof, NR Reading (GB); Andrew James Seeley, Bristol (GB)

(73) Assignee: Edwards Limited, Crawley, West Sussex (GB)

( * ) Notice: Subject to any disclaimer, the term of this patent is extended or adjusted under 35 U.S.C. 154(b) by 67 days.

(21) Appl. No.: 12/937,358

(22) PCT Filed: Mar. 24, 2009

(86) PCT No.: PCT/GB2009/050268
§ 371 (c)(1),
(2), (4) Date: Mar. 8, 2011

(87) PCT Pub. No.: WO2009/127846
PCT Pub. Date: Oct. 22, 2009

(65) Prior Publication Data
US 2011/0171743 A1    Jul. 14, 2011

(30) Foreign Application Priority Data
Apr. 14, 2008    (GB) .................................. 0806730.8

(51) Int. Cl.
*G01N 33/00*    (2006.01)
(52) U.S. Cl.
USPC ........... 436/124; 436/139; 436/141; 436/161; 436/171; 436/173; 436/181; 73/23.2

(58) Field of Classification Search
USPC ................. 436/124, 139, 141, 161, 171, 173, 436/174, 181; 422/83, 89; 73/23.2
See application file for complete search history.

(56) References Cited

U.S. PATENT DOCUMENTS

| | | | |
|---|---|---|---|
| 3,485,577 A * | 12/1969 | Kraus | 423/241 |
| 3,926,560 A | 12/1975 | Gentry | |
| 4,198,208 A | 4/1980 | Lerner et al. | |
| 5,242,668 A * | 9/1993 | Leman | 423/241 |
| 6,423,284 B1 * | 7/2002 | Arno et al. | 423/240 R |
| 6,602,480 B1 * | 8/2003 | Mori | 423/240 S |
| 2002/0051132 A1 | 5/2002 | Ohno et al. | |
| 2006/0065120 A1 * | 3/2006 | Clements et al. | 95/233 |
| 2010/0290966 A1 * | 11/2010 | Seeley | 423/239.1 |

FOREIGN PATENT DOCUMENTS

| | | | |
|---|---|---|---|
| GB | 2353034 | * | 2/2001 |
| JP | 63 027736 A | | 2/1988 |
| JP | 63 247655 A1 | | 10/1988 |
| WO | 2003082444 A1 | | 10/2003 |

* cited by examiner

*Primary Examiner* — Maureen Wallenhorst

(57) ABSTRACT

A method of measuring the concentration of a halogen in a gas stream using measurement means unsuitable for the direct measurement of halogens in a gas stream includes the step of passing a gaseous conversion compound to the halogen containing gas stream to convert the halogen to a detectable gaseous compound.

10 Claims, 3 Drawing Sheets

DETECTION OF HALOGENS

BACKGROUND OF THE INVENTION

The present invention relates to methods and apparatus for the detection of halogens, in particular fluorine.

The processing steps of silicon wafers for the manufacture of semiconductors use a wide range of precursor gases.

Precursor gases have very short residence times in a process chamber. Consequently, much of the gas is unused and any remaining process chemicals or their by-products are conveyed from the chamber by vacuum pumps to abatement equipment were they are destroyed to prevent their release into the environment.

Chamber cleaning processes and other wafer etch processing steps use gases such as $NF_3$, $SF_6$, perfluoroalkanes (PFCs) and Fluorine. These gases are either activated remotely and then passed to the chamber, or activated within the chamber, to produce fluorine radicals which etch silicon based deposits from the chamber walls or the surface of the wafer. As well as the reaction of the radicals with silicon oxide a certain percentage will also recombine to form "sink" PFC compounds, such as $CF_4$, or react to form diatomic fluorine molecules. These reaction by-products need to be destroyed due to their respective high global warming potential and toxicity.

When carrying out abatement of gases, such as those exhausted from an etch process, post abatement equipment exhaust gas analysis is often needed to ensure that the equipment is working properly and that each of the gases is being destroyed to below allowable legal limits.

Gases such as PFCs are easily measured and monitored using techniques such as infrared spectrometry, gas chromatography and continuous flow mass spectrometry. However there are several problems determining the presence of fluorine, and other halogens, in the exhaust gases with these techniques.

Due to their homonuclear diatomic structure the stretching vibration of the bond in the halogens $F_2$, $Cl_2$ and $Br_2$ does not cause a change in dipole moment and as such they are not detectable by infra red spectroscopy.

Due to the corrosive nature of the halogens, techniques such as gas chromatography require costly specialist columns which may not be suitable for the simultaneous detection of PFCs.

Similarly, cross sensitivity of mass spectrometers to other gases often present in semiconductor exhaust streams, such as argon and water vapour, interferes with the measurement of fluorine. In addition, prolonged exposure to corrosive gases such as halogens can often damage the delicate spectrometer instrumentation.

JP 63-27736 describes a method of passing a fluorine containing gas stream through a column of sulphur to convert the fluorine to $SF_6$, which is then analysed by infrared spectroscopy. However, by this method the user is not able to determine whether all the fluorine has been converted to $SF_6$. In order to be confident that the complete conversion of the fluorine had occurred a user would require either a long reaction column or very fine sulphur, which would cause problems with the conductance of the gas stream through the column.

Another example is that described in JP 63-247655 in which a gas stream containing fluorine is first passed through a column of potassium chloride to form a gas stream containing hydrochloric acid, which is subsequently passed through a column of potassium iodide to form a gas stream containing iodine. The liberated iodine can then be optically analysed. However, this technique is laborious and expensive, requiring two conversion steps, and in addition it is not possible to ensure that all the fluorine in the gas stream has been converted.

A further method of detecting the concentration of fluorine is that described in US20020051132 in which an exhaust gas stream containing fluorine and a hydrofluorocarbon (HFC) gas are passed through a solution containing a metal iodide. The fluorine reacts with the metal iodide to liberate iodine which is then analysed using light in the 460 nm to 520 nm region.

BRIEF SUMMARY OF THE INVENTION

The present invention provides a method of measuring the concentration of a halogen in a gas stream using measurement means unsuitable for the direct measurement of halogens in a gas stream comprising the step of passing a gaseous conversion compound to the halogen containing gas stream to convert the halogen to a detectable gaseous compound.

By this method the gaseous conversion compound reacts with the halogen in the gas stream converting the halogen to a gaseous compound which is directly detectable and analysed by the detection means. This is advantageous over the prior methods in that the conversion reactions occur in the gas phase, thus removing the complications arising from passing the halogen containing gas stream through either solid bed or liquid based reactors.

The concentration of halogen in the gas stream is then, in the first instance, calculated from the measured concentration of the detectable compound.

The halogen in the gas stream is preferably chlorine or fluorine and more preferably the halogen is fluorine. The conversion compounds ethene, the chloro or bromo methanes, or the bromo or chloro ethanes when passed to the fluorine containing gas stream rapidly react with fluorine to form fluoroethane, fluoromethane, or fluoroethane respectively. The conversion compound is preferable ethene due to its high reactivity with halogens and low global warming potential.

Hence, when using infrared spectroscopy as the detection means the strongly infrared active carbon-fluorine bond of the fluorinated alkanes formed in the conversion reaction will be readily detectable with its absorption intensity proportional to the concentration of fluorinated alkane present in the gas stream. Thus, the original concentration of fluorine in the gas stream can be calculated based on the know stoichiometry of the reaction between the fluorine and the gaseous conversion compound. For example the conversion reaction of fluorine with ethene will proceed according to the reaction:

$$C_2H_{4(g)} + F_{2(g)} \rightarrow C_2H_4F_{2(g)} \tag{1}$$

Similarly, when the measurement means is a gas chromatograph the concentration of the fluorinated alkane will now be readily detectable without the need for a specialist corrosion resistant column.

Also when the measurement means is a mass spectrometer the fluorinated alkane will be easily detectable without the argon and water cross sensitivity problems or associated risks to the sensitive instrumentation observed with prolonged exposure to a corrosive gas.

An excess of the gaseous conversion compound should be passed to the halogen containing gas stream. This is to ensure there is sufficient gaseous conversion compound in the gas stream to convert all of the halogen to a detectable gaseous compound. In addition, it is also advantageous to measure the concentration of any gaseous conversion compound in the gas stream. By simultaneously monitoring the change in concentration of the conversion compound and detectable compound the user is able to determine that all the halogen has been converted to a detectable compound by monitoring when the concentration of conversion compound falls to a constant level. In addition, it is also possible using this additional step to ensure that the original fluorine concentration, calculated from the concentration of detectable gaseous compound, is correct.

When the halogen is fluorine and the conversion compound is one of the chloro/bromo methanes or the chloro/bromo ethanes it is also advantageous to measure the concentration of hydrogen chloride or hydrogen bromide formed in the competition reaction between the fluorine and the gaseous conversion compound. This enables the user to do a further check on the amount of conversion compound that has reacted with the fluorine.

Similarly, when the halogen is chlorine and the conversion compound is one of the bromo methanes or the bromo ethanes it is advantageous to measure the concentration of hydrogen bromide formed in the competition reaction between the chlorine and the gaseous conversion compound.

By the methods described above it is possible to simultaneously monitor a larger range of the gaseous effluents, including halogens, exhausted from an abatement device attached to, for example, a semiconductor etching processes. Thus it is possible to simultaneously measure the concentration of fluorine and PFC, $NF_3$ and $SF_6$ that may be present in the exhaust gas stream using a single detection means.

BRIEF DESCRIPTION OF THE SEVERAL VIEWS OF THE DRAWINGS

Preferred features of the present invention will now be described with reference to the accompanying drawings, in which.

DETAILED DESCRIPTION OF THE INVENTION

Figure 1:
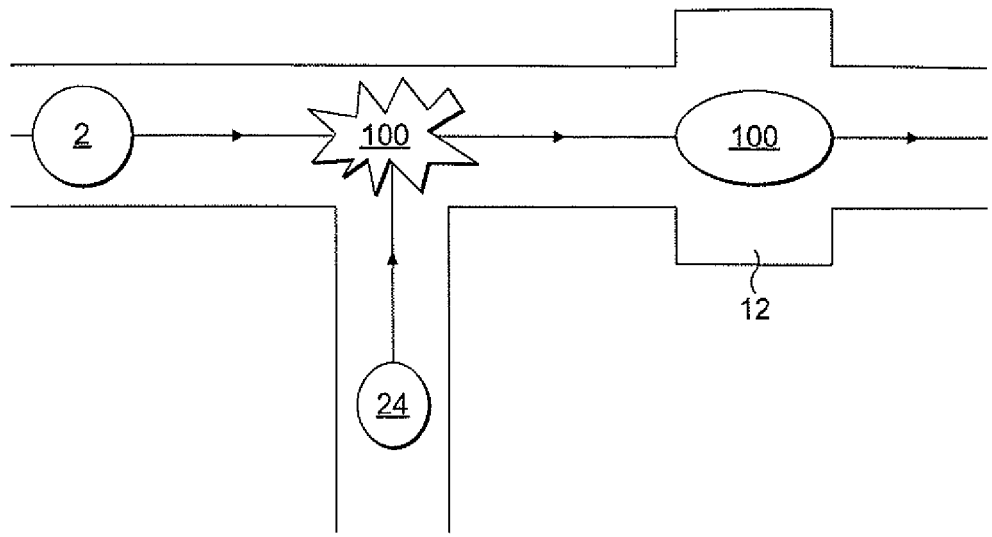
FIG. 1 is a schematic representation of the present invention.

With reference first to FIG. 1, a gaseous conversion compound (24), for example, ethene is passed to a halogen containing gas stream (2). The gas stream (2) may be, for example, the exhaust stream from an abatement device employed on a semiconductor etch process and contain gases such as fluorine and $NF_3$. The conversion compound (24) reacts with the halogen to produce detectable gaseous compound (100) which may be analysed by detection means (12).

Figure 2:
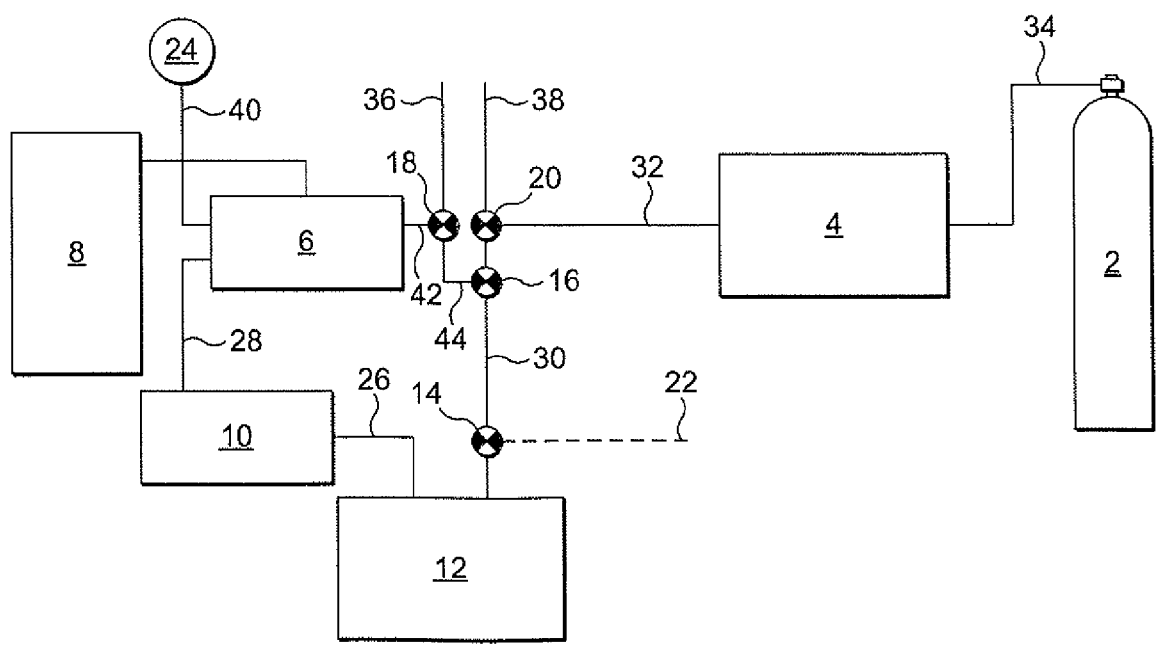
FIG. 2 is a schematic diagram of an example of a test apparatus used for qualifying the present invention.

With reference now to FIG. 2, the test apparatus comprised a fluorine containing gas stream (2) conveyed to dilution apparatus (4) via conduit (34). The source of gas stream (2) was a cylinder of 2% fluorine in nitrogen. The dilution apparatus (4) comprised a set of high sensitivity mass flow controllers which were able to accurately add diluent nitrogen to the fluorine containing gas stream to achieve a desired fluorine concentration.

The dilution apparatus (4) was in communication with three-way valve (20) via conduit (32). Three-way valve (20) was also in communication with both detection means (12), via conduit (30), and an exhaust line (38). The detection means (12) was a Multigas 2030 Fourier transform infrared spectrometer with a 5 meter internal gas cell. Conduit (30) also comprised three way valve (14) which was connected to a source of nitrogen purge gas (22).

Detection means (12) was in communication with the inlet of a diaphragm pump (10) via conduit (26). The outlet of the pump (10) was in communication with a 2 liter heated reaction chamber (6) via conduit (28).

A source of conversion gas (24) was in communication with reaction chamber (6) via conduit (40). The source of conversion gas (24) was a 100 cc syringe containing 500 microliters of pure ethene in 40 cc of nitrogen. The exhaust of chamber (6) was in communication with three-way valve (18) via conduit (42).

A Genysis mass spectrometer (8) was also in communication with chamber (6).

Three-way valve (18) was also both in communication with valve (16), via conduit (44), and an exhaust conduit (36).

The conduits (34, 32, 30, 26, 28, 40, 42 and 44) were all formed of inert PTFE tubing heated to 100° C.

Figure 3:
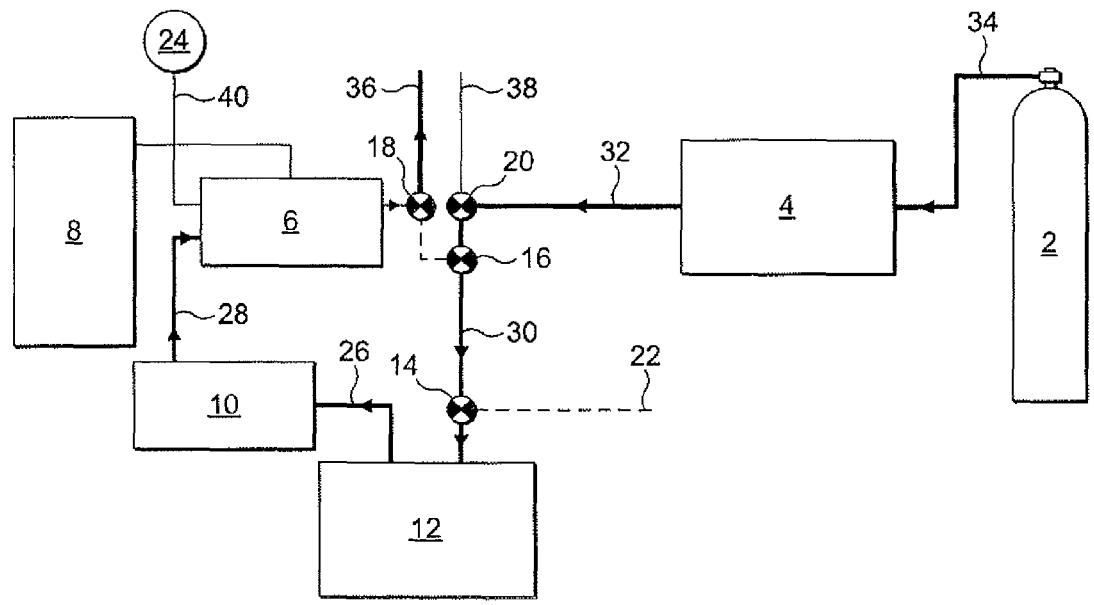
FIG. 3 is a schematic diagram of the test apparatus of FIG. 2 indicating the pre-conversion gas flow path used for qualifying the present invention.

In use, and turning initially to FIG. 3, a gas stream of 2% fluorine in nitrogen was passed to the dilution apparatus (4) in which the desired concentration of fluorine was set by adjusting the amount of diluent nitrogen added to the gas stream. The diluted fluorine containing gas stream passed from the dilution apparatus (4) to valve (20) which was set to direct the gas along conduit (30) to the spectrometer (12). The diaphragm pump (10) conveyed the gas from the spectrometer (12) to the reaction chamber (6) from which the gas exited via conduit (42) and was directed to exhaust conduit (36) by valve (18).

The fluorine containing gas stream was passed through the apparatus, as shown in FIG. 3, for approximately 5 to 10 minutes to ensure that a steady state of the desired fluorine concentration had been reached throughout the apparatus.

Figure 4:
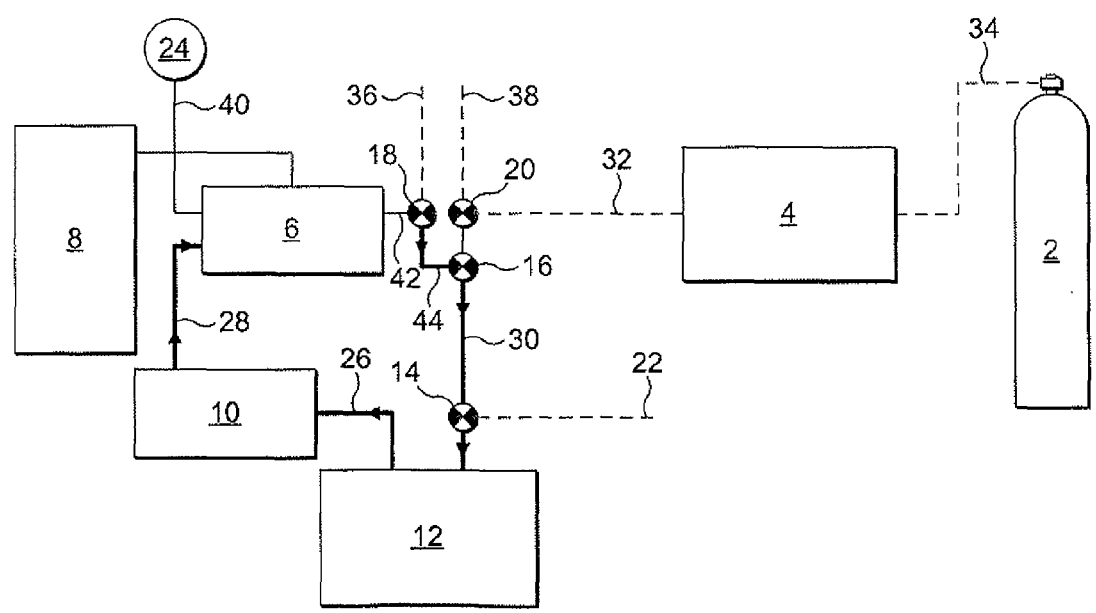
FIG. 4 is a schematic diagram of the test apparatus of FIG. 2 indicating the post-conversion gas flow path used for qualifying the present invention.

Once a steady state was considered to have been reached valves (18) and (16) were operated to direct the gas flow into the closed loop system along conduits (44, 42, 28, 26 and 30) shown in FIG. 4. The flow of diluted fluorine containing gas stream was then stopped, or directed to the exhaust conduit (38) by valve (20). 500 microliters of pure ethene in 40 cc of nitrogen was then injected into the chamber (6) via conduit (40). The presence and concentration of 1,2-difluoroethane was then monitored with the infrared spectrometer (12) by monitoring the carbon-fluorine bond in the 1030 to 1120 $cm^{-1}$ region. When the concentration of 1,2-difluoroethane detected by the spectrometer (12) had reached a maximum value a reading was taken. The concentration of ethene in the gas stream was also monitored.

The concentration of each of the gaseous species in the gas stream was also monitored by mass spectrometer (8).

Figure 5:
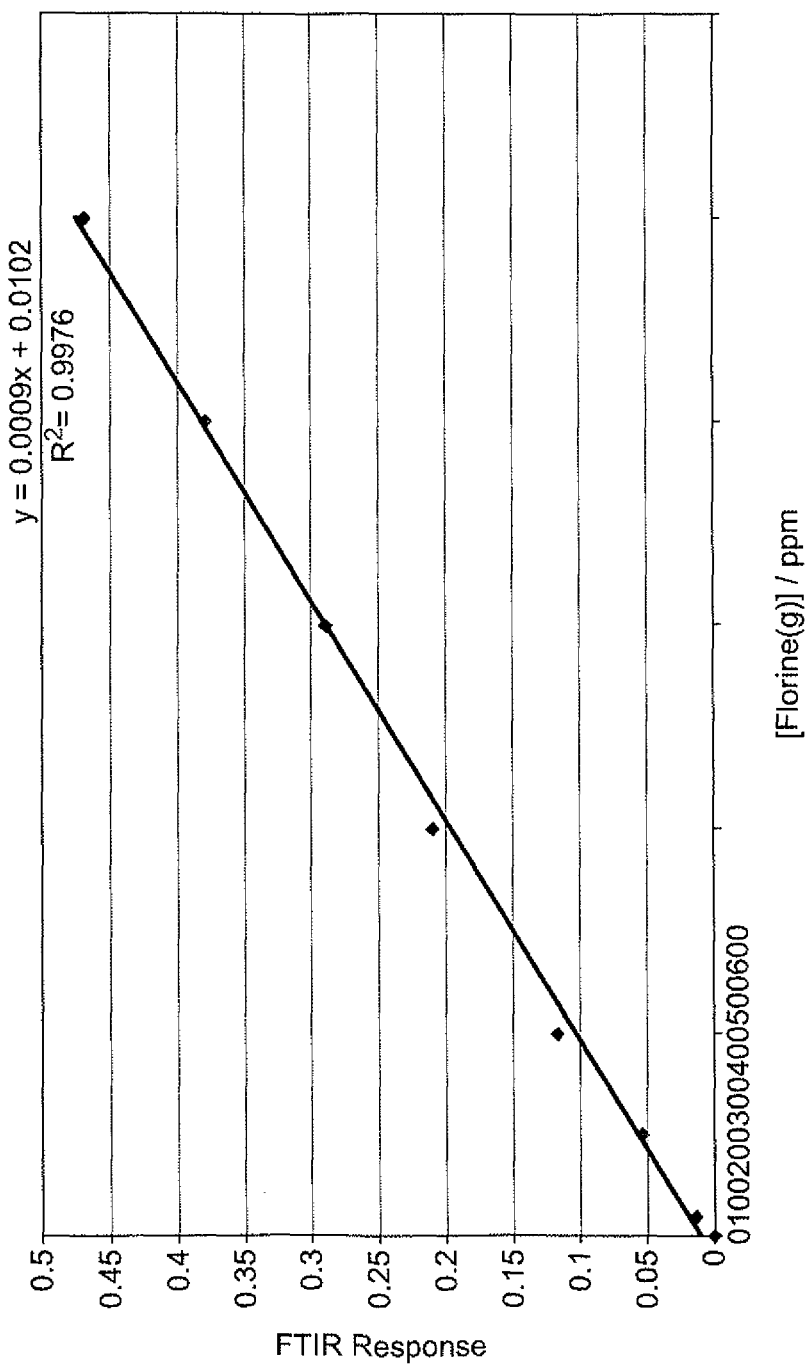
FIG. 5 is a graph indicating the response of an FTIR spectrometer vs. original fluorine concentration in the gas stream in a test carried out with the apparatus of FIG. 1 according to the present invention.

The gas flow through the apparatus was then switched back to the open loop system shown in FIG. 3 and the same experiment repeated for a range of fluorine concentrations. The response of the spectrometer (12) vs. original fluorine concentration is shown in FIG. 5. It can be seen that a linear relationship was observed.

It was also possible to detect a correlation between the fall in concentration of ethene with the rise in concentration of 1,2-difluoroethane (not shown).

The invention claimed is:

1. A method of measuring a concentration of a halogen in a gas stream, comprising the step of:
    passing a gaseous conversion compound to the halogen containing gas stream to convert the halogen to a detectable gaseous compound;
    measuring a concentration of the gaseous conversion compound and a concentration of the detectable gaseous compound; and
    when the concentration of the gaseous conversion compound falls to a constant level, calculating a concentration of the halogen in the gas stream based on the measured concentration of the detectable gaseous compound and a known stoichiometry of a reaction between the halogen and the gaseous conversion compound.

2. The method according to claim 1, wherein the halogen in the gas stream is one of Fluorine or Chlorine.

3. The method according to claim 2, wherein the conversion compound is at least one of ethene, a chloro-methane, a bromo-methane, a chloro-ethane and a bromo-ethane.

4. The method according to claim 1, wherein a constant flow of gaseous conversion compound is passed to the halogen containing gas stream.

5. The method according to claim 1, wherein the gaseous conversion compound is passed to the halogen containing gas stream at timed intervals.

6. The method according to claim 1, wherein the method also comprises measuring the concentration of gaseous conversion compound remaining unconverted in the gas stream.

7. The method according to claim 1, wherein the gaseous conversion compound is at least one of chloro-methanes, bromo-methanes, chloro-ethanes, and bromo-ethanes and wherein the method also comprises measuring a concentration of hydrogen-halide formed in a reaction between fluorine and the gaseous conversion compound.

8. The method according to claim 1, wherein the gaseous conversion compound is ethene.

9. The method according to claim 1, wherein the measuring is carried out by an infrared spectrometer, a gas chromatograph, or a mass spectrometer.

10. The method according to claim 1, wherein the halogen containing gas stream also contains at least one additional detectable gaseous compound.

* * * * *